United States Patent [19]
Smith et al.

[11] Patent Number: 5,996,596
[45] Date of Patent: Dec. 7, 1999

[54] METHOD AND APPARATUS FOR CLEANING OPHTHALMIC LENSES AND BLOCKS

[75] Inventors: Kenneth L. Smith, Porum; Todd R. Strope, Tulsa, both of Okla.

[73] Assignee: Coburn Optical Industries, Inc., Tulsa, Okla.

[21] Appl. No.: 08/974,703

[22] Filed: Nov. 19, 1997

[51] Int. Cl.⁶ ............................................. B08B 3/02
[52] U.S. Cl. .................... 134/61; 134/78; 134/147; 134/135
[58] Field of Search .................. 134/56 R, 57 R, 134/135, 184, 186, 147, 160, 164, 78, 61

[56] References Cited

U.S. PATENT DOCUMENTS

| | | | |
|---|---|---|---|
| 793,825 | 7/1905 | Curry et al. | 134/135 |
| 902,861 | 11/1908 | Danenhower | 134/78 |
| 1,042,242 | 10/1912 | Lock | 134/164 |
| 1,329,863 | 2/1920 | Snure | 134/135 |
| 2,167,185 | 7/1939 | Preston | 134/78 |
| 2,535,111 | 12/1950 | Wishart | 134/78 |
| 2,815,624 | 12/1957 | Faler et al. | 134/78 |
| 3,871,395 | 3/1975 | Murry | 134/107 |
| 4,370,991 | 2/1983 | Lindvall | 134/164 |
| 4,561,902 | 12/1985 | Lee | 134/147 |
| 5,499,642 | 3/1996 | Uchino | 134/147 |

FOREIGN PATENT DOCUMENTS

| | | | |
|---|---|---|---|
| 415140 | 7/1925 | Germany | 134/135 |
| 60-137717 | 7/1987 | Japan | 134/61 |

*Primary Examiner*—Frankie L. Stinson
*Attorney, Agent, or Firm*—Frank J. Catalano

[57] ABSTRACT

A process and machine for cleaning ophthalmic lenses and blocks heats a washing solution in a wash tank and a rinsing solution in a rinse tank to approximately 140° F. Ultrasonic wave agitation is then initiated in the solutions. A set of lenses or blocks is immersed in the ultrasonically agitated washing solution for approximately one-half the predetermined time of the wash cycle. Mechanical agitation of the immersed set of lenses or blocks is initiated in the ultrasonically agitated washing solution for the remainder of the predetermined time of the wash cycle. The set of lenses or blocks is then raised above the washing solution for a predetermined drip period. The set of lenses or blocks is then immersed in the ultrasonically agitated rinsing solution for approximately one-half the predetermined time of the rinse cycle. Mechanical agitation of the immersed set of lenses or blocks is initiated in the ultrasonically agitated rinsing solution for the remainder of the predetermined time of the rinse cycle. The set of lenses or blocks is then raised above the rinsing solution for a predetermined drip period.

3 Claims, 6 Drawing Sheets

METHOD AND APPARATUS FOR CLEANING OPHTHALMIC LENSES AND BLOCKS

BACKGROUND OF THE INVENTION

This invention relates generally to ophthalmic lenses and more particularly concerns a method and apparatus for cleaning ophthalmic lenses in preparation for application of a scratch resistant coating and for cleaning blocks used in the generation and finishing of ophthalmic lenses for reuse.

Presently, ophthalmic lenses and blocks are cleaned in a substantially manual procedure involving a number of workers located at a series of two or three wash stations and two or three rinse stations with the lens or block to be cleaned being passed through each station. The process is time consuming and labor intensive. A six percent lens scrap rate is typical of the process, the lenses not being usable either because of damage caused directly to the lens in the cleaning process or because the lens was not properly cleaned before the coating was applied.

In addition to the inefficiency of the process itself, the multiple bath process uses expensive, space consuming stations. Therefore, only one such system is generally used in a lab. However, because of the number of steps involved in the lens making process, it is inconvenient that the cleaning process must be performed at one location in the lab.

It is, therefore, an object of this invention to provide a method and apparatus for cleaning ophthalmic lenses and blocks which reduces the manpower necessary in the cleaning process. Another object of this invention is to provide a method and apparatus for cleaning ophthalmic lenses and blocks which reduces the space required for the physical location of a cleaning station. Another object of this invention is to provide a method and apparatus for cleaning ophthalmic lenses and blocks which makes the use of multiple cleaning stations in the same lab economically feasible. Yet another object of this invention is to provide a method and apparatus for cleaning ophthalmic lenses and blocks which reduces the lens scrap rate of the process.

SUMMARY OF THE INVENTION

In accordance with the invention, a process is provided for cleaning ophthalmic lenses and blocks. A washing solution is heated in a wash tank and a rinsing solution in a rinse tank to approximately 140° F. Ultrasonic wave agitation is then initiated in the solutions. A set of lenses or blocks is immersed in the ultrasonically agitated washing solution for approximately one-half the predetermined time of the wash cycle. Mechanical agitation of the immersed set of lenses or blocks is initiated in the ultrasonically agitated washing solution for the remainder of the predetermined time of the wash cycle. The set of lenses or blocks is then raised above the washing solution for a predetermined drip period. The set of lenses or blocks is then immersed in the ultrasonically agitated rinsing solution for approximately one-half the predetermined time of the rinse cycle. Mechanical agitation of the immersed set of lenses or blocks is initiated in the ultrasonically agitated rinsing solution for the remainder of the predetermined time of the rinse cycle. The set of lenses or blocks is then raised above the rinsing solution for a predetermined drip period. To accomplish this, a machine is provided which has a wash tank containing a quantity of chemical washing solution and a rinse tank containing a quantity of chemical rinsing solution. Heaters are used to raise the washing solution and the rinsing solution to a predetermined temperature. Ultrasonic transducers cause agitation of the heated washing and rinsing solutions. A mechanism is provided for rotating the holder from a load position above and between the tanks to a wash position with the set of lenses or blocks fully immersed in the washing solution and a rinse position with the set fully immersed in the rinsing solution. A computer controls the operation of the rotating mechanism to immerse the holder in the washing solution for approximately the first one-half of the predetermined time of the washing cycle, to mechanically agitate the holder in the washing solution for a remainder of the washing cycle, to raise the holder above the washing solution for the predetermined dripping period, to immerse the holder in the rinsing solution for approximately the first one-half of the predetermined time of the rinsing cycle, to mechanically agitate the holder in said rinsing solution for the remainder of the rinsing cycle and to raise the holder above the rinsing solution for the predetermined dripping period.

BRIEF DESCRIPTION OF THE DRAWINGS

Other objects and advantages of the invention will become apparent upon reading the following detailed description and upon reference to the drawings in which.

While the invention will be described in connection with a preferred method and embodiment, it will be understood that it is not intended to limit the invention to that method and embodiment. On the contrary, it is intended to cover all alternatives, modifications and equivalents as may be included within the spirit and scope of the invention as defined by the appended claims.

DETAILED DESCRIPTION

Figure 1:
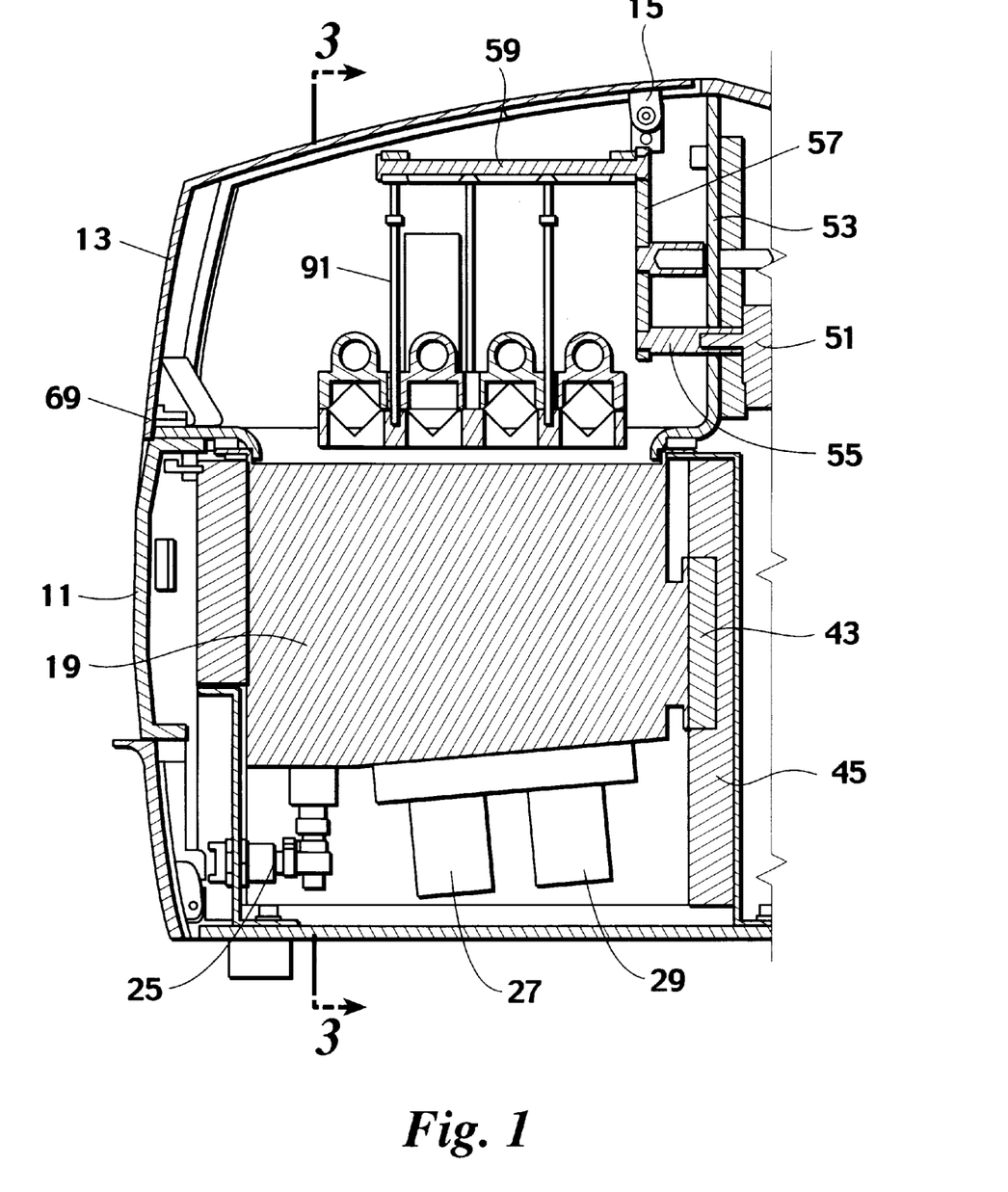
FIG. 1 is a side elevation view of a preferred embodiment of the ophthalmic lens and block cleaning machine.
Figure 3:
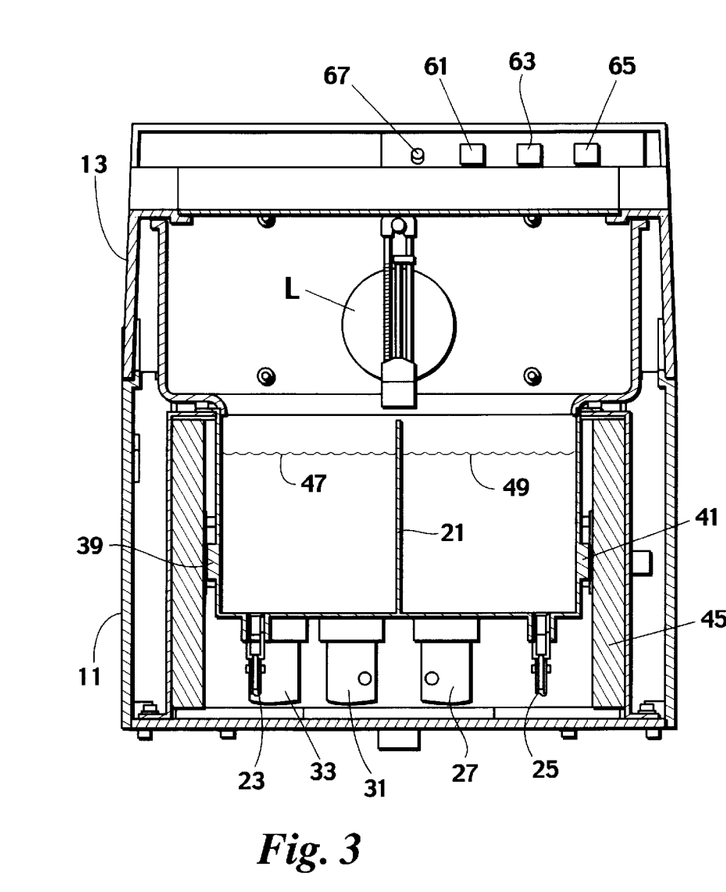
FIG. 3 is a cross-sectional view taken along the line 3—3 of FIG. 1.

Turning first to FIGS. 1 and 3, a preferred embodiment of a machine for cleaning ophthalmic lenses and blocks is illustrated with the dunking mechanism of the machine in its home or load position. As shown, the machine consists of a main enclosure 11 and a hinged lid 13, the hinges 15 being located at the upper rear portion of the lid 13. Within the enclosure 11, a wash tank 17 and a rinse tank 19 are mounted side by side with a common wall 21 between them. Each tank 17 and 19 is provided with a drain valve 23 and 25, respectively, for quick connect and disconnect to a drain hose (not shown). A plurality of ultrasonic transducers 27, 29, 31, 33, 35 and 37 (not all shown in these figures) are mounted on the bottom of the wash and rinse tanks. As shown, the tanks 17 and 19 have an angled bottom so as to facilitate drainage to the valves 23 and 25. A first heater 39 is mounted on the left side of the wash tank 17, a second heater 41 is mounted on the right side of the rinse tank 19 and a third heater 43 extends across the rear of both tanks 17 and 19. The tanks 17 and 19 and the heaters 39, 41 and 43 are surrounded by insulation 45. The tanks 17 and 19 are also provided with visible wash and rinse lines 47 and 49, respectively, which indicate the desired levels of washing and rinsing solutions.

A gear motor 51 mounted in the back of the machine on a support plate 53 extending upwardly to the top of the lid 13 has its shaft 55 connected by a linkage arm 57 to the dunking arm 59 of the machine. The dunking arm 59 extends forwardly from the linkage arm 57 and the motor shaft 55 is centered between the wash and rinse tanks 17 and 19 so that, with the shaft 55 in its home position, the linkage arm extends vertically above the shaft 55 and the tanks 17 and 19 with the longitudinal axis of the dunking arm 59 aligned with the common wall 21 between the tanks 17 and 19. The machine is provided with a lens cycle button 61, a block cycle button 63, a stop button 65 and a trouble light 67. Preferably, the lens cycle button and block cycle button 61 and 63 include green indicator lights which will be on when the machine is in readiness to run either of these cycles. The lens cycle and blank cycle are identical except in duration, the lens cleaning process requiring a longer process time than the block cleaning cycle. The stop button 65, preferably red, enables the operator to interrupt the operation of the machine at any time. The trouble light 67, preferably amber, is indicative of an error or power failure in the system. The lid 13 is also provided with a magnetic reed switch 69 which prevents the operation of the machine when the lid 13 is open.

Figure 2:
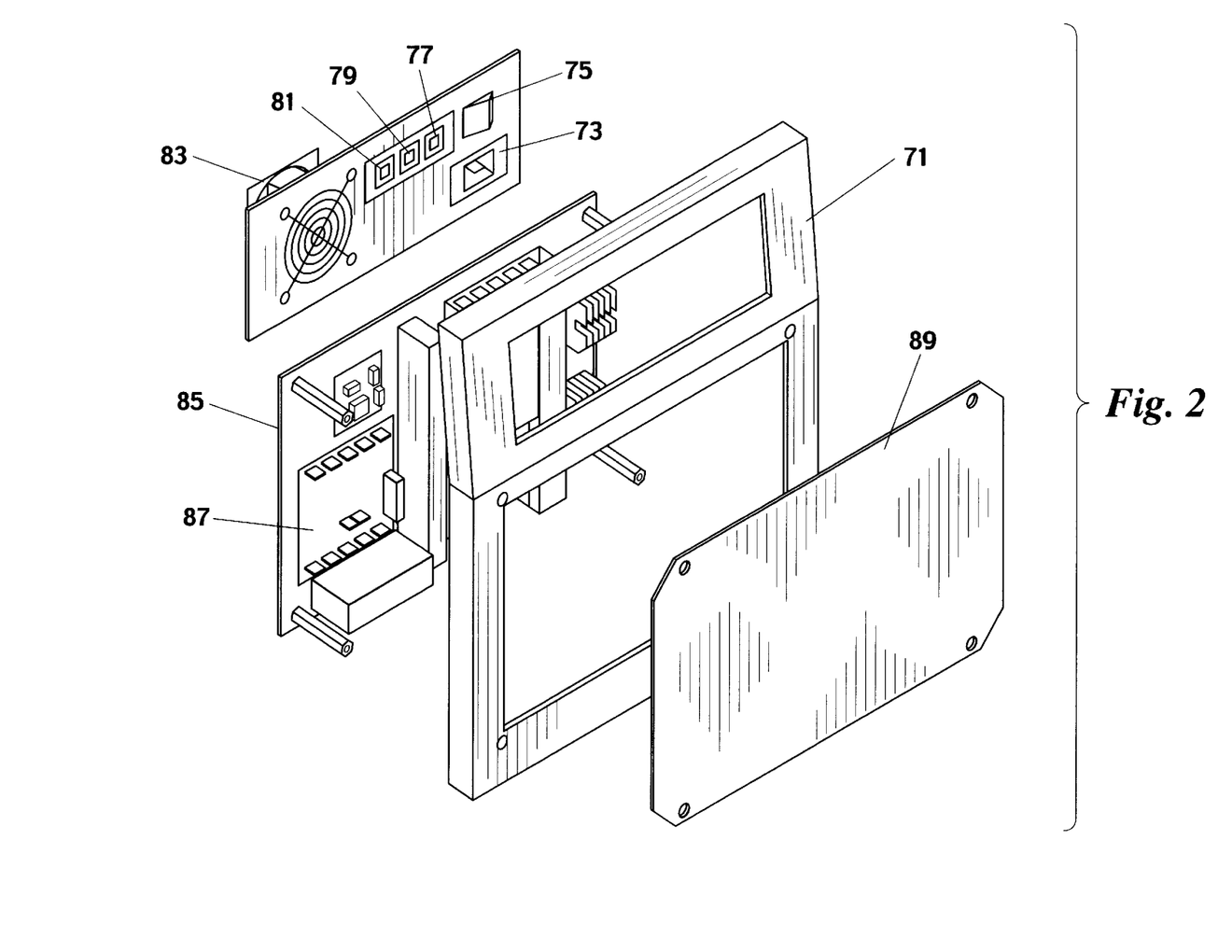
FIG. 2 is a perspective assembly view of a preferred embodiment of the rear panel of the machine of FIG. 1.

Turning now to FIG. 2, the back panel 71 of the machine contains the power cord connector 73, power switch 75, one amp, four amp and ten amp circuit breakers 77, 79 and 81, respectively, and an exhaust fan 83. The one amp circuit breaker 77 protects the control system of the machine, the four amp circuit beaker 79 protects the ultrasonic drive system and the ten amp circuit breaker 81 protects the cleaning solution heaters 39, 41 and 43. The ten amp circuit breaker 81 will automatically trip if an over temperature condition occurs. The exhaust fan 81 pulls fresh air into the enclosure to cool the internal components of the machine and to exhaust the heated air out the back of the machine. An electrical panel 85 in the back panel 71 supports the CPU board 87 which includes an EPROM chip which provides the operating software for the machine. The back panel 71 is covered by a removable access panel 89.

Figure 4:
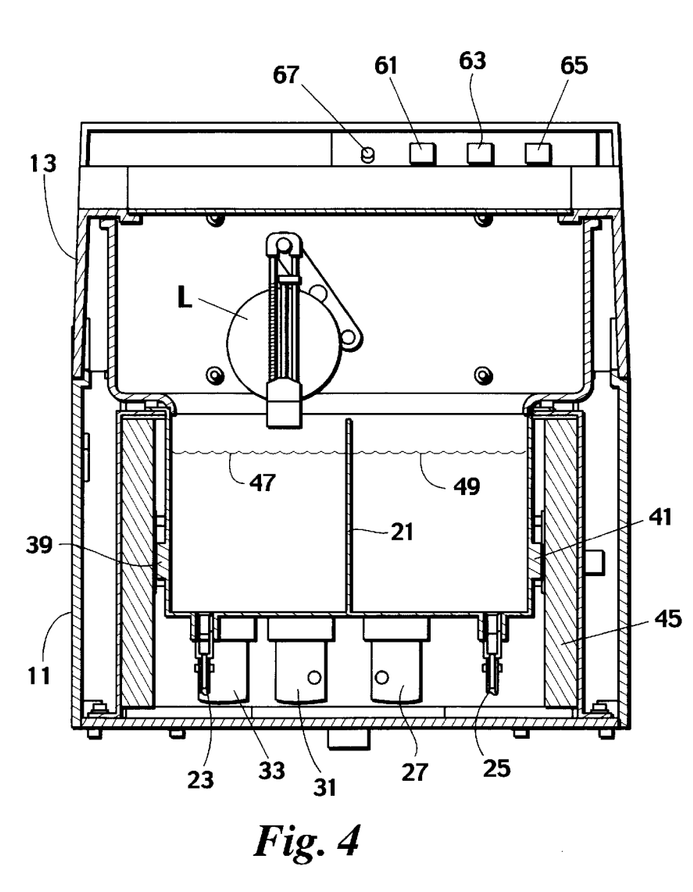
FIG. 4 is a cross-sectional view taken along the line 3—3 of FIG. 1 with the dunking arm of the machine rotated to initiate insertion of a lens into the wash tank.
Figure 5:
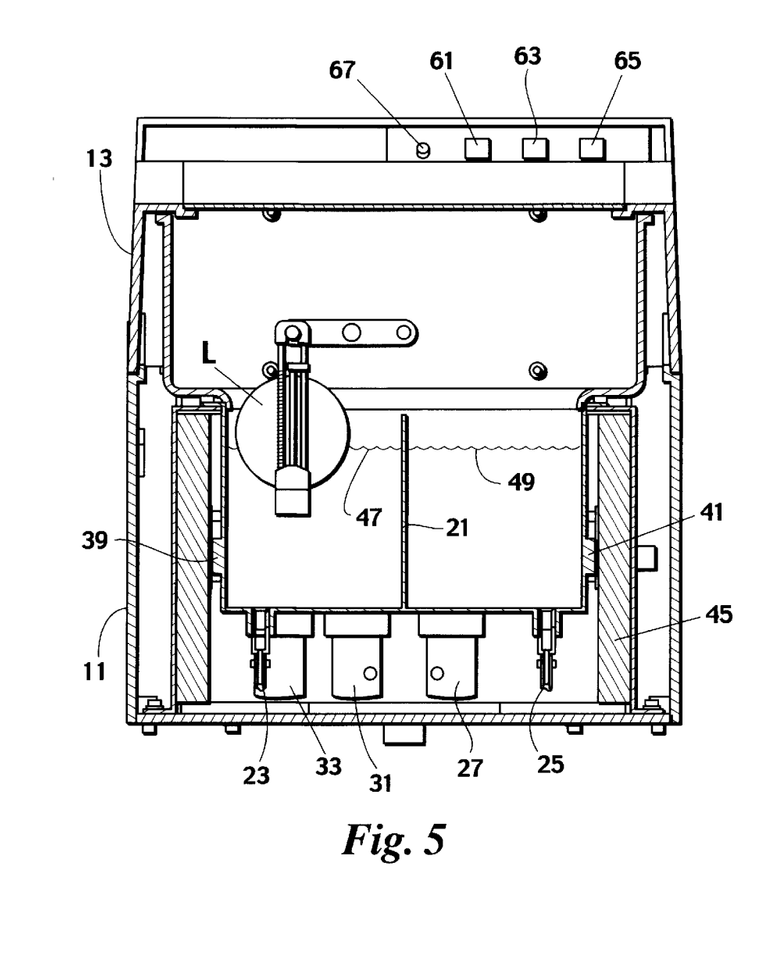
FIG. 5 is a cross-sectional view taken along the line 3—3 of FIG. 1 with the dunking arm of the machine rotated to significant immersion of the lens into the wash tank.
Figure 6:
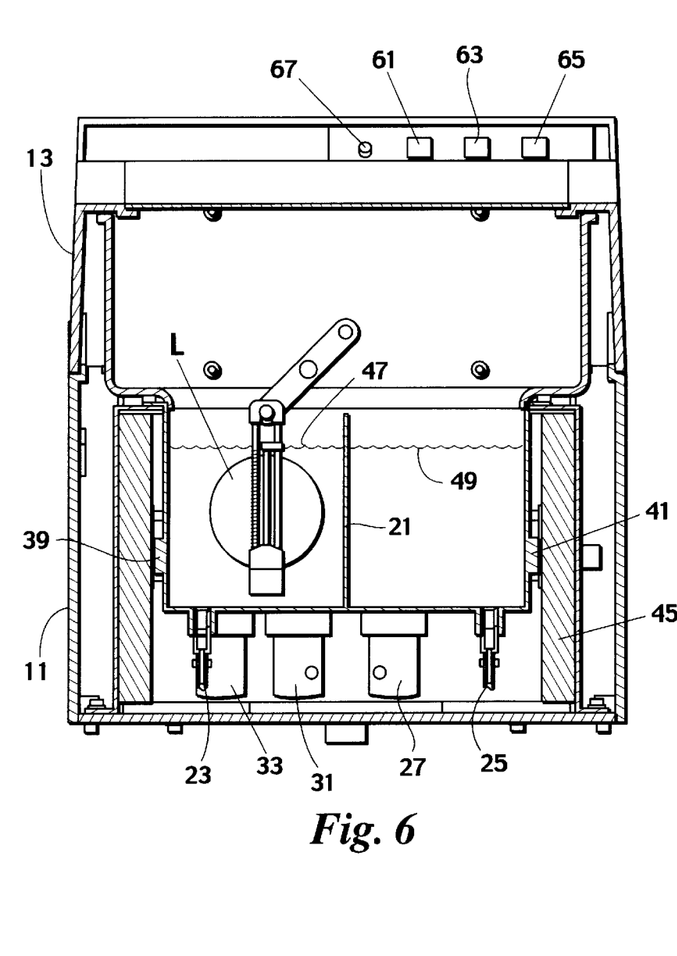
FIG. 6 is a cross-sectional view taken along the line 3—3 of FIG. 1 with the dunking arm of the machine rotated to fully immerse the lens in the wash tank.
Figure 7A:
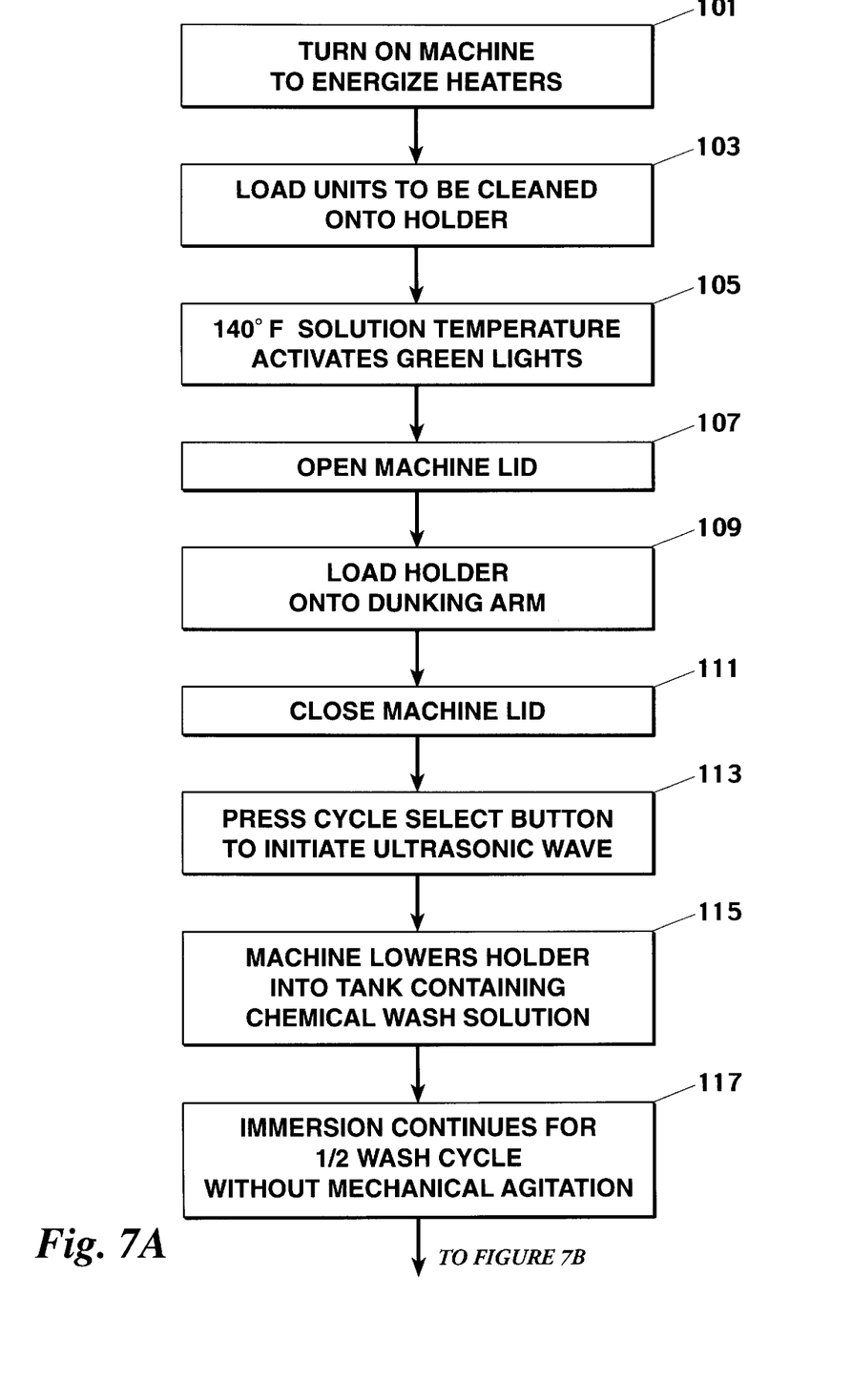
FIGS. 7A and 7B are block diagrams illustrating the steps of the cleaning process.
Figure 7B:
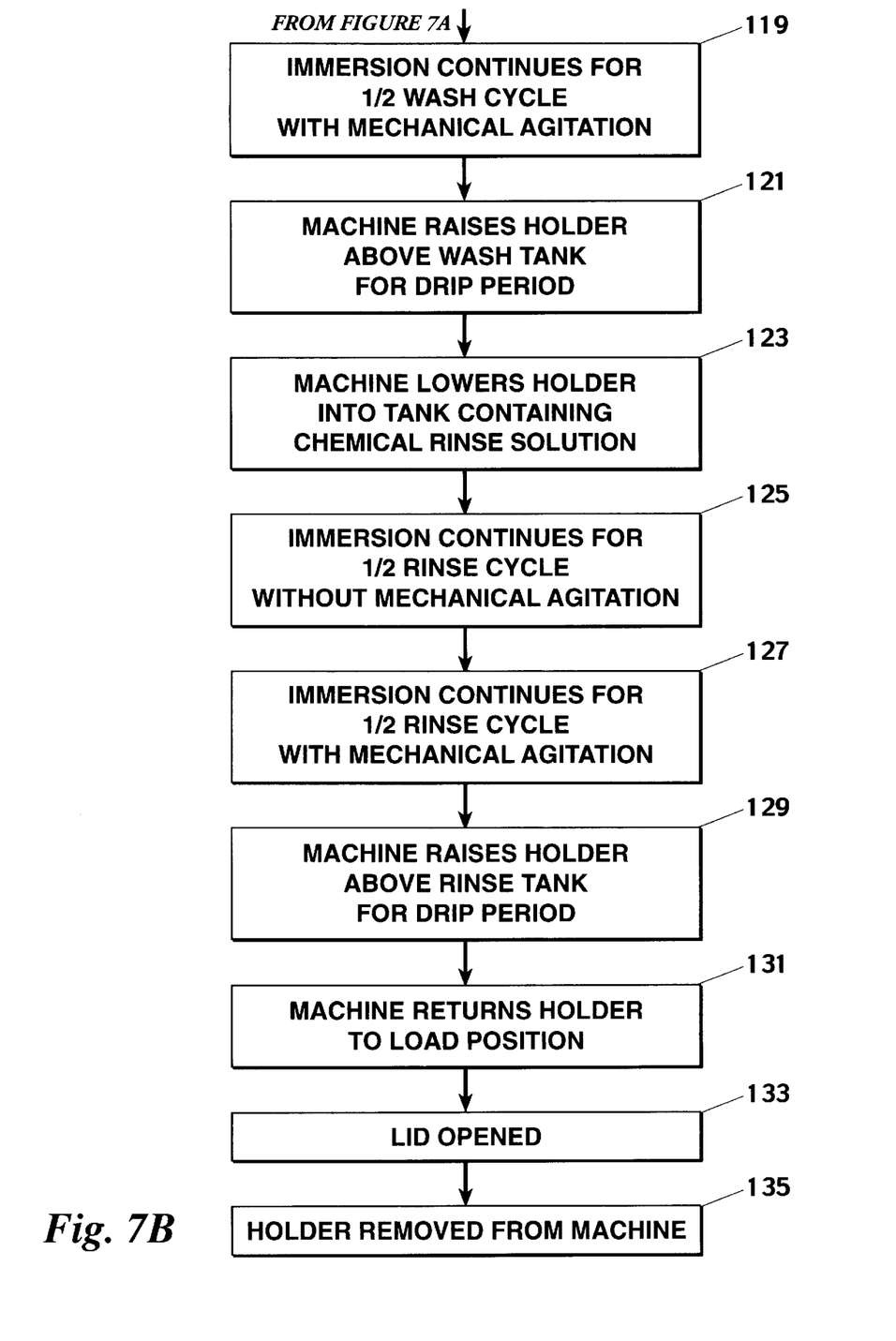

The operation of the machine can best be understood in relation to FIGS. 7A and 7B. The wash tank 17 and the rinse tank 19 are filled to their wash and rinse lines 47 and 49, respectively, with the appropriate cleaning solution. Preferably, the washing solution includes a mixture of Lens Cleaner Plus available from Coburn Optical Industries, Inc. of Muskogee, Okla., 409 by Clorox Company of Oakland, Calif. and deionized water. The rinse solution preferably consists of a combination of 409 by Clorox Company of Oakland, Calif. and deionized water. Each tank preferably holds 8/10 of a gallon of solution to a depth sufficient to cover any lens L or block inserted into the tanks 17 and 19. With electrical power available to the machine, the power switch 75 is operated in the first step 101 to turn on the machine and energize the heaters 39, 41 and 43. The operator proceeds to the next step 103 in which the units to be cleaned are loaded onto a holder 91. Typically, the holder 91 is capable of supporting four lenses L or blocks (not shown). In the next step 105, the machine monitors the solution temperature to activate the green lights on the lens cycle button 61 and the block cycle button 63 which indicates that the machine is operable in either cycle. It should be noted that operation of these cycles cannot be initiated until a nominal temperature of 140° F. has been attained. However, once cycle initiation occurs, operation will continue provided that the temperature is maintained between a minimum of 130° F. and a maximum of 160° F. If the temperature exceeds 140° F., the machine will automatically turn off and must be manually reset. The trouble light 67 will indicate the existence of the problem. A similar result occurs if the temperature drops below the 130° F. minimum. When the green lights of the lens cycle and block cycle buttons 61 and 63 are activated, the operator opens the machine lid and loads the holder 91 onto the dunking arm 59 in the steps 107 and 109. At this point, the loaded holder 91 is vertically aligned above the common wall 21 between the tanks 17 and 19. With the holder 91 mounted on the dunking arm 59, the operator next closes the machine lid 111 and then presses a cycle select button 61 or 63 to initiate ultrasonic wave 113 in the tanks 17 and 19. Ultrasonic waves of a frequency range of 40 to 60,000 KHz and preferably at 40,000 KHz have been found to be quite suitable for the purpose. Operating wattages of 150 to 250 watts have also been found acceptable, though this could vary depending upon the length of cycle time desired. The operator, who has either all lenses or all blocks onto a single holder, selects the lens cycle button 61 which will result in the longer lens cleaning cycle time required or the block cycle button 63 which will result in the shorter block cycle time required. Typically, a lens cleaning cycle will run for one minute with approximately fifteen seconds spent in each of the non-mechanically agitated and mechanically agitated wash times and in the non-mechanically and mechanically agitated rinse times. In the block cleaning cycle these segments are reduced from fifteen seconds to approximately 7½ seconds each. Once the cycle select button has been pressed 113, the machine automatically lowers the holder 91 into the tank 17 containing the chemical wash solution 115. In the next step 117, the immersion of the holder 91 and the units which it contains continues for one-half the wash cycle without mechanical agitation 117. That is, when the cycle select button is pressed 113, the machine is in the home condition illustrated in FIG. 3. The machine then automatically lowers the holder 91 so that the machine rotates from the home position downwardly and to the left as indicated in FIG. 4 through the condition in which the linkage arm 57 is horizontal as shown in FIG. 5 to its lowermost position with the lens L fully immersed below the wash line 47 of the wash tank 17 as shown in FIG. 6. The machine maintains the condition illustrated in FIG. 6 throughout the first half of the wash cycle, providing immersion without mechanical agitation 117. When approximately half of the wash cycle has elapsed, the immersion continues in step 119 except that the remaining half of the wash cycle immersion continues with mechanical agitation. That is, the gear motor 51 causes its shaft 55 to oscillate to raise and lower the holder 91 in the wash tank 17 between approximately the conditions shown in FIGS. 5 and 6. When the second half of the wash cycle is completed, the machine next raises the holder 91 above the wash tank 17 as shown in FIG. 4 for the drip period 121 in which the chemical wash solution can drip from the lens L or block into the wash tank 17 without introducing contaminants into the rinse tank solution. When the drip period has concluded, the machine lowers the holder 91 into the tank 19 containing the chemical rinse solution 123. Again, immersion continues in step 125 for approximately one-half the rinse cycle without mechanical agitation and then, in the next step 127, immersion continues for the remaining approximately one-half rinse cycle with mechanical agitation. When the rinse cycle is completed, in the next step 129, the machine raises the holder 91 above the rinse tank 19 for the drip period to allow drying of the holder 91 and its contents. When the drip period is concluded, in the next step 131, the machine returns the holder 91 to its home or load position as shown in FIG. 3. The operator then opens the lid at step 133 and removes the holder from the machine at step 135, completing the cleaning process. The operation of the gear motor 51 during the rinse cycle is essentially a mirror image of its operation in the wash cycle.

It is essential to the process above described that all four phases of the process must be exercised in both the wash and rinse cycles. That is, the process includes cleaning which results from a chemical bath, electronically controlled heat levels, ultrasonic wave bombardment and agitated or oscillated dipping of the lens or block to be cleaned. The absence of any one of these phases results in an inadequate cleaning process. For example, without agitation, the polishing compound on a lens will not be entirely removed. On the other hand, without proper temperature control, ultrasonic wave bombardment and chemical solution, wax will not be completely removed from the lens or block. Furthermore, without the combination of the proper chemical solution and ultrasonic wave bombardment an oily film will remain on a lens. However, when all of these phases are applied in the wash and rinse cycles, the resulting process and machine are such that one machine can perform the work of two people using the previously known cleaning processes and that the operation of the machine requires only half the time of one operator.

Thus, it is apparent that there has been provided, in accordance with the invention, a method and apparatus for cleaning ophthalmic lenses and blocks that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. An apparatus for cleaning one of a set of ophthalmic lenses and blocks mounted in a holder comprising:

a wash tank containing a quantity of chemical washing solution;

a rinse tank containing a quantity of chemical rinsing solution;

means for heating said washing solution and said rinsing solution to a predetermined temperature;

means for causing ultrasonic agitation of said heated washing solution and said heated rinsing solution;

means for rotating said holder from a load position above and between said tanks to a wash position with the one of a set fully immersed in the washing solution and a rinse position with the one of a set fully immersed in the rinsing solution;

means for controlling the operation of said rotating means to immerse the holder in said washing solution for approximately a first ½ of a predetermined time of a washing cycle, to mechanically agitate the holder in said washing solution for a remainder of said washing cycle, to raise the holder above said washing solution for a predetermined dripping period, to immerse the holder in said rinsing solution for approximately a first ½ of a predetermined time of a rinsing cycle, to mechanically agitate the holder in said rinsing solution for a remainder of said rinsing cycle and to raise the holder above said rinsing solution for a predetermined dripping period.

2. An apparatus for cleaning one of a set of ophthalmic lenses and blocks mounted in a holder comprising:

a wash tank containing a quantity of chemical washing solution;

a rinse tank containing a quantity of chemical rinsing solution;

means for heating said washing solution and said rinsing solution to a predetermined temperature;

means for causing ultrasonic agitation of said heated washing solution and said heated rinsing solution;

means for rotating said holder from a load position above and between said tanks to a wash position with the one of a set fully immersed in the washing solution and a rinse position with the one of a set fully immersed in the rinsing solution;

means for controlling the operation of said rotating means to immerse the holder in said washing solution for approximately a first ½ of a predetermined time of a washing cycle, to oscillate said rotating means to mechanically agitate a holder in said washing solution for a remainder of said washing cycle, to raise the holder above said washing solution for a predetermined dripping period, to immerse the holder in said rinsing solution for approximately a first ½ of a predetermined time of a rinsing cycle, to oscillate said rotating means to mechanically agitate the holder in said rinsing solution for a remainder of said rinsing cycle and to raise the holder above said rinsing solution for a predetermined dripping period.

3. An apparatus for cleaning one of a set of ophthalmic lenses and blocks mounted in a holder comprising:

a wash tank containing a quantity of chemical washing solution;

a rinse tank containing a quantity of chemical rinsing solution;

means for heating said washing solution and said rinsing solution to a predetermined temperature;

means for causing ultrasonic agitation of said heated washing solution and said heated rinsing solution;

an arm adapted at one end for engagement with the holder and rotatable about a pivot axis at another end to permit rotation of said holder from a load position above and between said tanks to a wash position with the one of a set fully immersed in the washing solution and a rinse position with the one of a set fully immersed in the rinsing solution;

means for rotating said arm about said pivot axis; and means for controlling the operation of said rotating means to immerse the holder in said washing solution for approximately a first ½ of the predetermined time of a washing cycle, to oscillate rotation of said arm about said pivot axis to mechanically agitate the holder in said washing solution for a remainder of said washing cycle, to raise the holder above said washing solution for a predetermined dripping period, to immerse a holder in said rinsing solution for approximately a first ½ of the predetermined time of a rinsing cycle, to oscillate rotation of said arm about said pivot axis to mechanically agitate the holder in said rinsing solution for a remainder of said rinsing cycle and to raise the holder above said rinsing solution for a predetermined dripping period.

* * * * *